(12) United States Patent  
Alsaifi

(10) Patent No.: US 10,765,309 B1
(45) Date of Patent: Sep. 8, 2020

(54) MULTIFUNCTIONAL OTOSCOPE

(71) Applicant: Ziad A. Alsaifi, Boise, ID (US)

(72) Inventor: Ziad A. Alsaifi, Boise, ID (US)

(*) Notice: Subject to any disclaimer, the term of this patent is extended or adjusted under 35 U.S.C. 154(b) by 566 days.

(21) Appl. No.: 14/931,662

(22) Filed: Nov. 3, 2015

(51) Int. Cl.
*A61B 1/227* (2006.01)
(52) U.S. Cl.
CPC ................................. *A61B 1/227* (2013.01)
(58) Field of Classification Search
CPC ............................... A61B 1/227; A61B 1/2275
USPC ................... 600/200; D24/135, 137
See application file for complete search history.

(56) References Cited

U.S. PATENT DOCUMENTS

| | | | | |
|---|---|---|---|---|
| 3,110,304 | A | * | 11/1963 | Hartman .............. A61B 1/227 600/200 |
| 3,840,004 | A | | 10/1974 | Heine |
| 4,662,360 | A | | 5/1987 | Phillips |
| 4,785,796 | A | * | 11/1988 | Mattson ............... A61B 1/227 362/109 |
| D333,702 | S | * | 3/1993 | Hufman ....................... D24/135 |
| 5,390,663 | A | * | 2/1995 | Schaefer ............. A61B 1/227 600/200 |
| D406,339 | S | * | 3/1999 | Stacks ....................... D24/137 |
| 5,916,150 | A | | 6/1999 | Sillman |
| 5,919,130 | A | * | 7/1999 | Monroe ............... A61B 1/227 600/129 |
| D421,123 | S | * | 2/2000 | Kugler ....................... D24/137 |
| 6,106,457 | A | * | 8/2000 | Perkins ............ A61B 1/00041 396/312 |
| 6,165,125 | A | * | 12/2000 | Elliott ............. A61B 1/00087 600/184 |
| 6,213,938 | B1 | | 4/2001 | Cook |
| 6,416,464 | B2 | * | 7/2002 | Elliott ............. A61B 1/00087 600/184 |
| 7,354,399 | B2 | | 4/2008 | Strom et al. |
| 8,062,216 | B2 | | 11/2011 | Raghuprasad |
| 8,374,683 | B2 | * | 2/2013 | Stone ............. A61B 1/00142 600/179 |

(Continued)

FOREIGN PATENT DOCUMENTS

WO 1986001992 A1 4/1986

OTHER PUBLICATIONS

Medit Veterinary Endoscopy; Multi Use Veterinary Otoscope—Endoscope; available at http://endoscopy4vet.com/html/veterinary_otoscope.html (last accessed Nov. 8, 2016).

(Continued)

*Primary Examiner* — Eric S Gibson
(74) *Attorney, Agent, or Firm* — Parry IP PLLC; Jeffrey C. Parry

(57) ABSTRACT

An otoscope speculum can include forceps, a curette, or other instruments to allow healthcare providers to treat a patient while observing thought the otoscope lens. According to some embodiments, a flexible hinge on an otoscope speculum orients forceps jaws and allows the healthcare provider to close the forceps jaws by applying a squeezing force. In other embodiments, a curette on an otoscope speculum allows the healthcare provider to perform scraping operations on a patient. Embodiments of the present disclosure may be used to examine and/or treat a variety of orifices of a patient, including the ear. The various specula instruments may allow the healthcare provider to view the treatment through the otoscope lens while the instrument is in use.

15 Claims, 7 Drawing Sheets

(56) References Cited

U.S. PATENT DOCUMENTS

2011/0166421 A1* 7/2011 Katiraei .............. A61B 1/227
                                                                         600/200

OTHER PUBLICATIONS

Preferred Products; Hotchkiss Otoscope; available at http://www.preferredproduct.com/hotchkiss-operating-otoscope/ (last accessed Nov. 8, 2016).

* cited by examiner

MULTIFUNCTIONAL OTOSCOPE

BACKGROUND

Technical Field

The present disclosure relates generally to otoscope tools. In particular, the present disclosure relates to methods and devices for performing examination or scraping, debriding, removal of foreign body, and/or like operations on a patient's ear or other orifice.

Description of Related Art

An otoscope is a tool that is commonly used by physicians and other healthcare providers to examine the ear of a patient. A typical otoscope comprises a head and a handle. An otoscope head commonly includes a magnifying lens and a light source, while the handle is typically a rigid handle connected to the otoscope head. The front of the otoscope head typically has an attachment point for a speculum, which is commonly a plastic disposable frustum-shaped piece shaped to roughly conform to the patient's ear canal and allow the healthcare provider to examine the patient's ear by viewing through the magnifying lens and the speculum. An otoscope light source may typically be powered by rechargeable or disposable batteries in the otoscope handle or by a power cord plugged into a wall outlet.

Often, a healthcare provider may examine a patient's ear with an otoscope in response to a manifestation of symptoms such as ear pain, hearing loss, obstruction, or to screen for various illnesses.

BRIEF DESCRIPTION OF THE DRAWINGS

Non-limiting and non-exhaustive embodiments of the present disclosure are described with reference to the following figures, wherein like reference numerals refer to like parts throughout the various views unless otherwise specified.

Figure 1A:
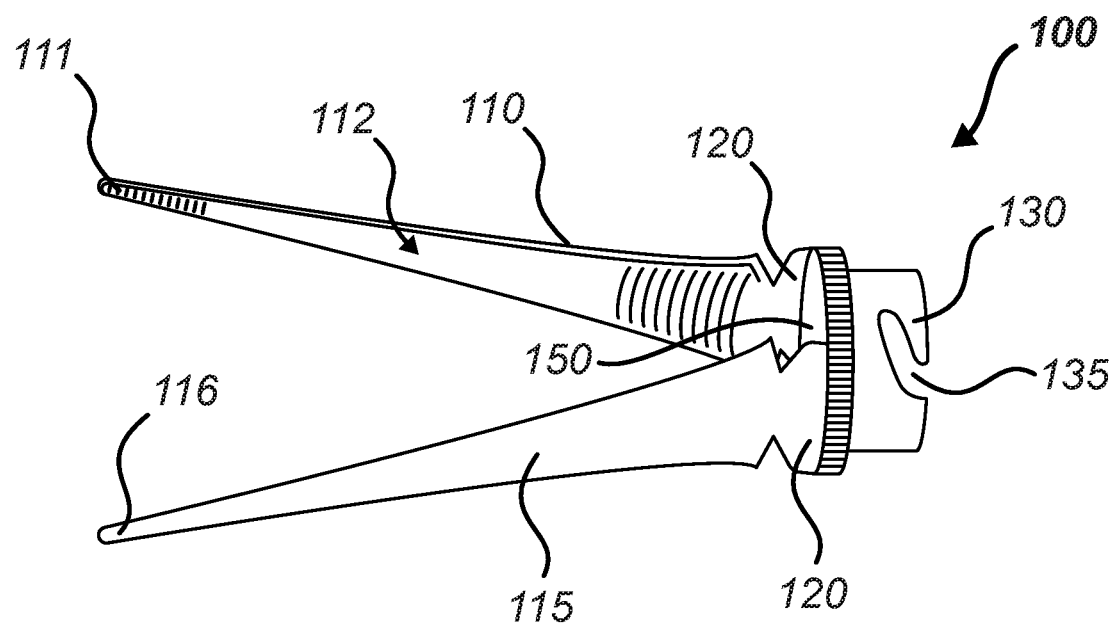
FIG. 1A depicts a perspective view of an otoscope attachment comprising forceps according to an embodiment of the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, reference is made to exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the spirit and scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

Embodiments of the present disclosure include methods and devices for examining and/or treating obstructions, foreign bodies, and the like within a patient's ear. As used herein, the term "patient" may include, but is not limited to, a person or animal that is the subject of medical care, attention, and/or testing. As would be understood by a person of ordinary skill in the art having the benefit of the present disclosure, the patient may be a human or virtually any type of animal.

Figure 1B:
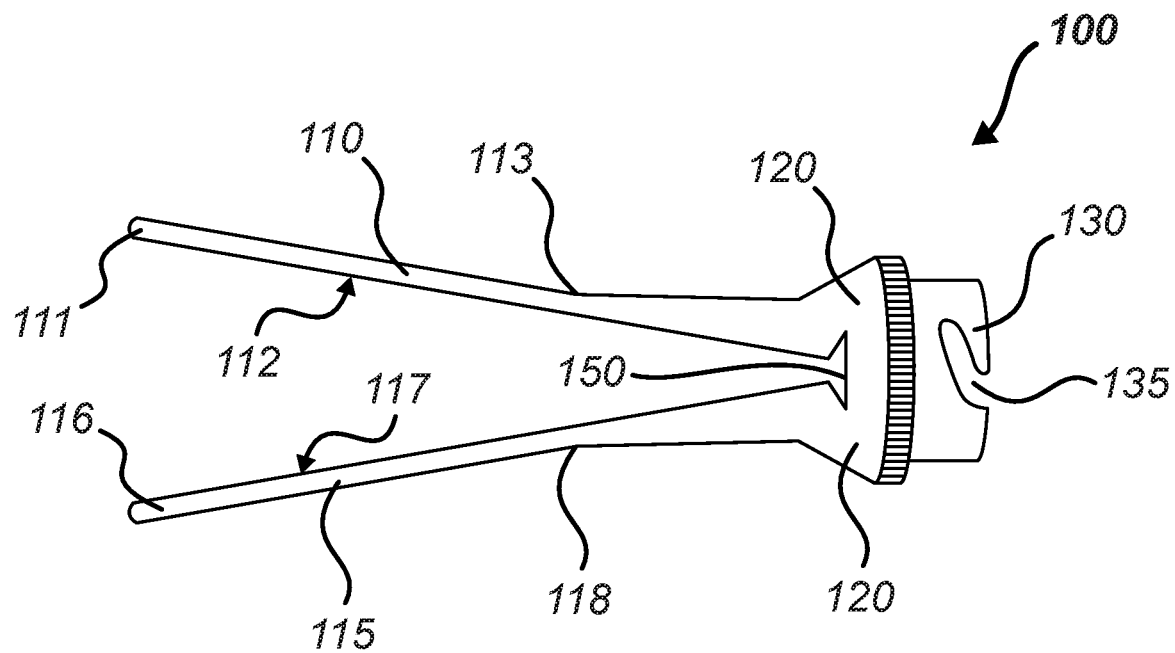
FIG. 1B depicts a side view of an otoscope attachment comprising forceps according to an embodiment of the present disclosure.

Referring to FIGS. 1A and 1B, embodiments of the present disclosure comprise an otoscope speculum 100 having forceps. According to various embodiments, otoscope speculum 100 may be attached to an otoscope in front of the magnifying lens and light source (i.e., at the otoscope distal end). Otoscope speculum 100 comprises a pair of forceps jaws 110, 115 connected by compliant hinge 120 to an annular otoscope attachment end 130.

According to the embodiment depicted, jaws 110, 115 have clamping surfaces 111, 116. Embodiments of clamping surfaces 111, 116 include a knurled surface. In one embodiment, jaws 110, 115 each have inner concave surfaces 112, 117. In this embodiment, concave surfaces 112, 117 can allow light to pass through a cavity between and along the lengths of jaws 110, 115 even while jaws 110, 115 are closed or mostly closed. As a result, a healthcare provider can see between jaws 110, 115 along the length of jaws 110, 115 and can see objects near or at the distal end of jaws 110, 115 while using speculum 100 while viewing through the otoscope lens. In other embodiments, jaws 110, 115 have flat inner surfaces.

In one embodiment, jaws 110, 115 each include an outward bend 113, 118. Bend 113 and 118 may allow a healthcare provider to better grip objects while forceps jaws 110, 115 are closed. In other words, bend 113, 118 may provide an increase in clamping force relative to a straight jaw. In particular, bend 113, 118 causes a clamping force to extend from hinge 120 at a direction oblique to clamping surfaces 111, 116, which may act to maintain gripping pressure on objects within jaws 110, 115.

According to various embodiments, hinge 120 is manufactured from a flexible material that can deform as jaws 110, 115 close and open. Such types of hinges may be referred to as "living hinges." In one embodiment, hinge 120 comprises one or more sections of material that are thinned to permit bending along the hinge line. In embodiments, hinge 120 exerts a spring effect to open jaws 110, 115 while not squeezed together.

Otoscope attachment end 130 includes helical attachment slits 135 around the annular surface of otoscope attachment end 130 for engagement with corresponding projections on an otoscope. Speculum 100 may be secured to an otoscope by aligning slits 135 to the corresponding projections on an otoscope, sliding speculum toward the otoscope to engage the projections with each slit 135, and rotating speculum 100 to further engage the projections with slits 135. A friction fit between an inner surface of annular attachment end 130 and an outer surface of the otoscope may further secure speculum 100 to the otoscope. In embodiments, multiple attachment slits 135 may increase stabilization of the connection between speculum 100 and an otoscope. In other embodiments, specula can be attached to an otoscope by various additional means and mechanisms.

Figure 2A:
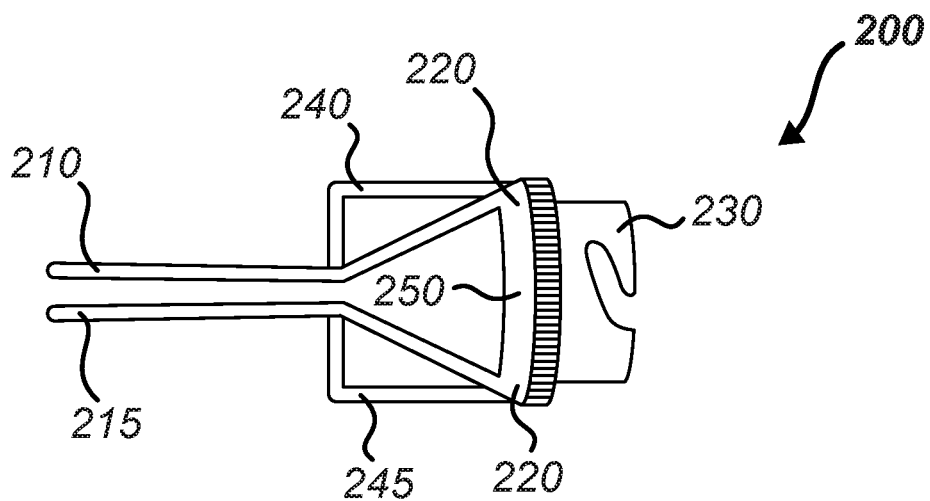
FIG. 2A depicts a side view of an otoscope attachment comprising open forceps having finger grip plates according to an embodiment of the present disclosure.
Figure 2B:
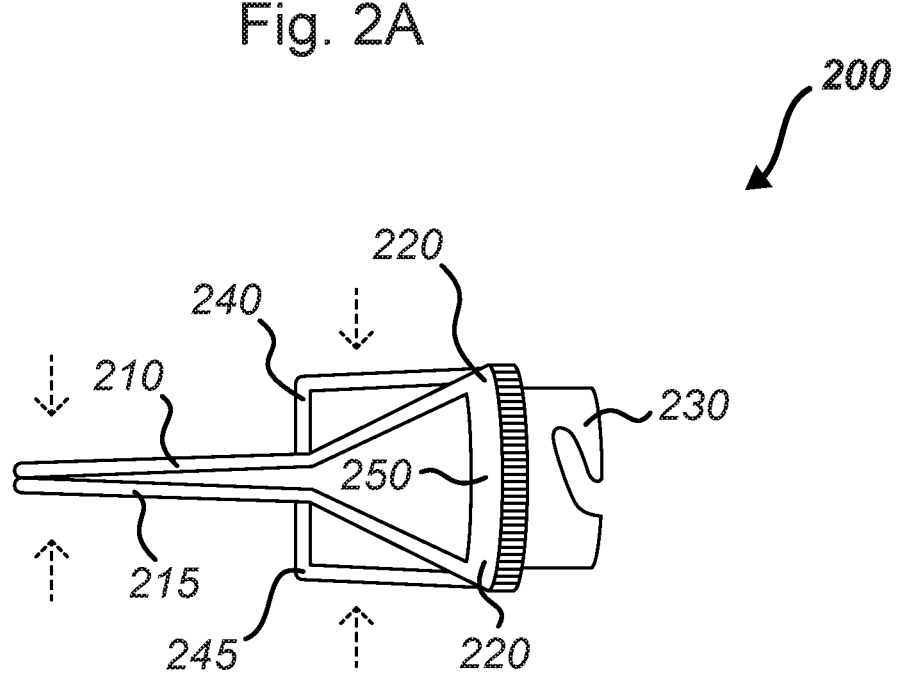
FIG. 2B depicts a side view of an otoscope attachment comprising closed forceps having finger grip plates according to an embodiment of the present disclosure.
Figure 2C:
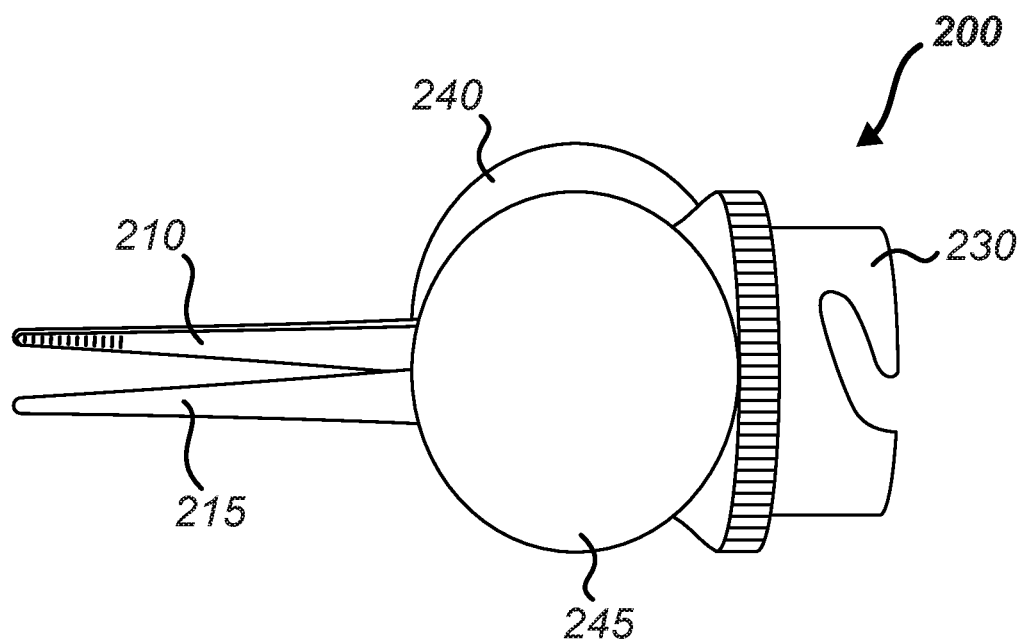
FIG. 2C depicts a top view of an otoscope attachment comprising forceps having finger grip plates according to an embodiment of the present disclosure.

Referring to FIGS. 2A, 2B, and 2C, one embodiment of the present disclosure comprises a speculum 200. As described above, speculum 200 comprises jaws 210, 215, hinge 220, and an annular attachment end 230 for attaching speculum 200 to an otoscope. Speculum 200 comprises finger grip plates 240, 245, where a squeezing force may be applied to close hinge 220, thereby causing jaws 210, 215 to close. As the squeezing force is released, hinge 220 can open back to its neutral, open state, thereby causing jaws 210, 215 to open. FIG. 2C depicts a lateral view of the speculum 200 depicted in FIGS. 2A and 2B.

Figure 2D:
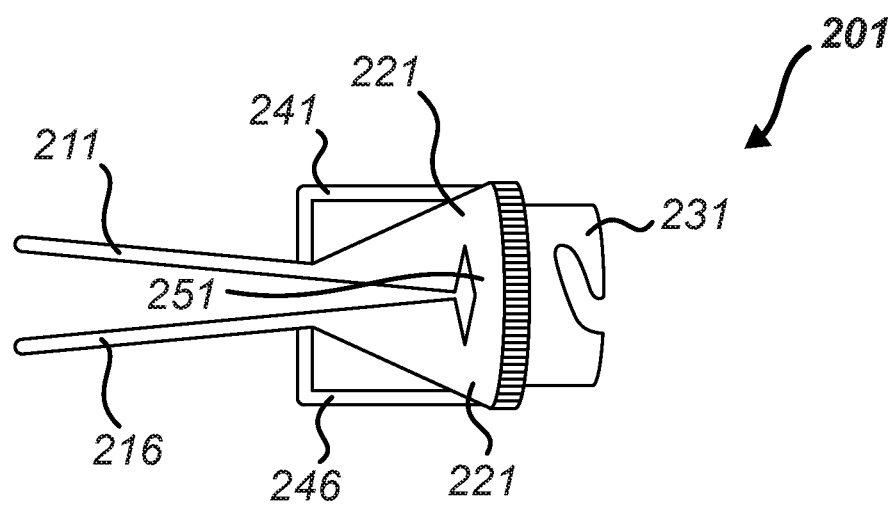
FIG. 2D depicts an otoscope attachment comprising forceps having finger grip plates according to a second embodiment of the present disclosure.

Referring to FIG. 2D, one embodiment of the present disclosure comprises a speculum 201. As described above, speculum 201 comprises jaws 211, 216, hinge 221, and an annular attachment end 231 for attaching speculum 201 to an otoscope. Speculum 201 comprises finger grip plates 241, 246, where a squeezing force may be applied to close hinge 221, thereby causing jaws 211, 216 to close. As the squeezing force is released, hinge 221 can open back to its neutral, open state, thereby causing jaws 211, 216 to open. In the embodiment depicted, speculum 201 comprises a funnel-shaped enclosure that partially conceals the light source of the attached otoscope. FIG. 2C depicts a lateral view of the speculum 201 depicted in FIG. 2D.

Figure 3A:
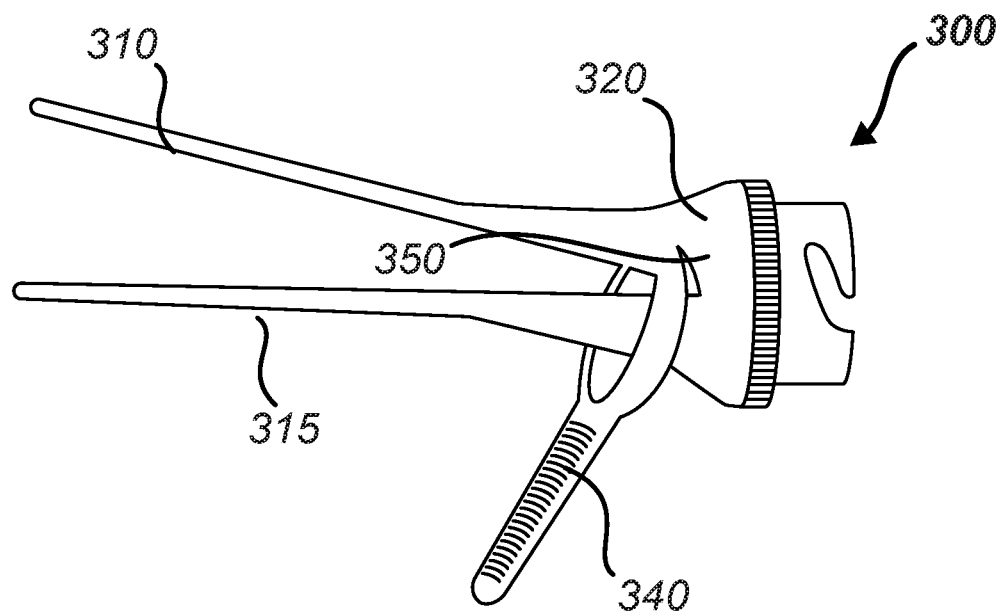
FIG. 3A depicts an otoscope attachment comprising open forceps having ergonomic finger grip plates according to an embodiment of the present disclosure.
Figure 3B:
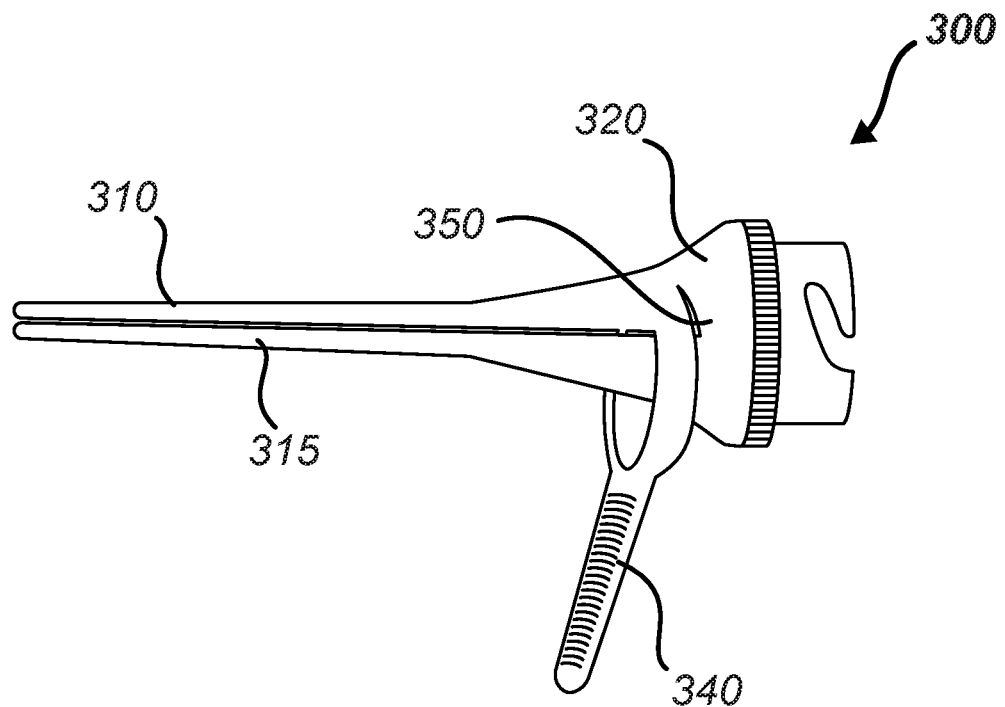
FIG. 3B depicts an otoscope attachment comprising closed forceps having ergonomic finger grip plates according to an embodiment of the present disclosure.

Referring to FIGS. 3A and 3B, speculum 300 includes a squeeze trigger 340 that, when pulled by a user, causes jaws 310, 315 to close. Hinge 320 can exert an opposing and/or opening force on jaws 310, 315. In alternative embodiments, a forceps hinge comprises a pivot pin adapted to allow forceps jaws to open and close. Some embodiments comprise a spring or flexible hinge to bias the forceps to an open position. Some embodiments comprise a spring or flexible hinge to bias the forceps to a closed position.

Figure 4:
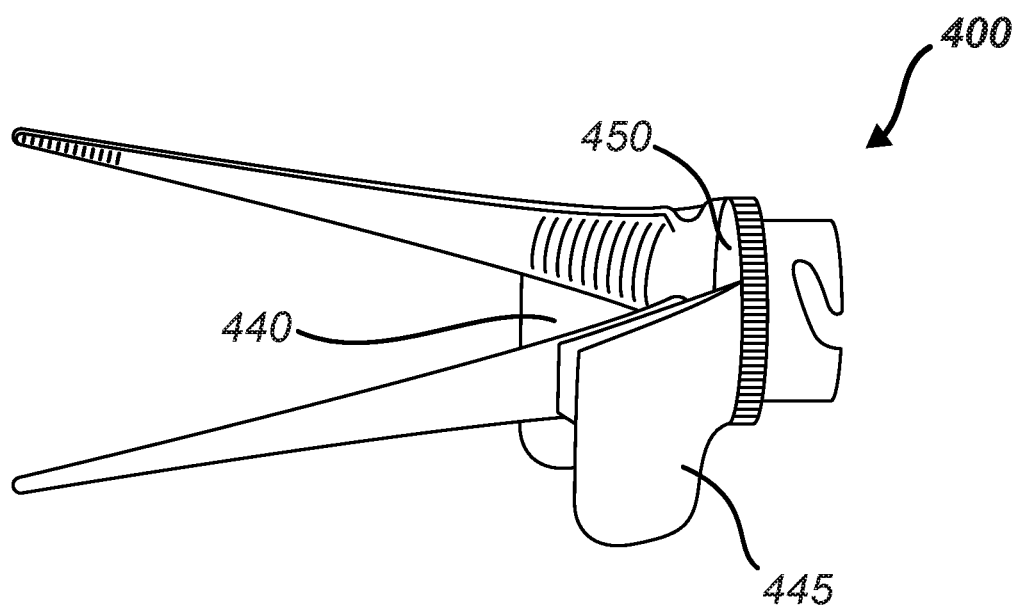
FIG. 4 depicts an otoscope attachment comprising forceps having a squeeze trigger according to an embodiment of the present disclosure.

Referring to FIG. 4, speculum 400 comprises finger grip plates 440, 445. According to one embodiment, finger grip plates 440, 445 have ergonomic features to increase comfort and/or ease of use.

According to various embodiments, specula may be manufactured out of plastics including, but not limited to, polyethylene, polypropylene, or combinations thereof. In some embodiments, specula may be manufactured by various injection molding operations as a single piece, or they may be manufactured as separate components and subsequently assembled. In embodiments, disposable specula may be intended for single use for hygienic and/or sterility reasons.

Figure 5:
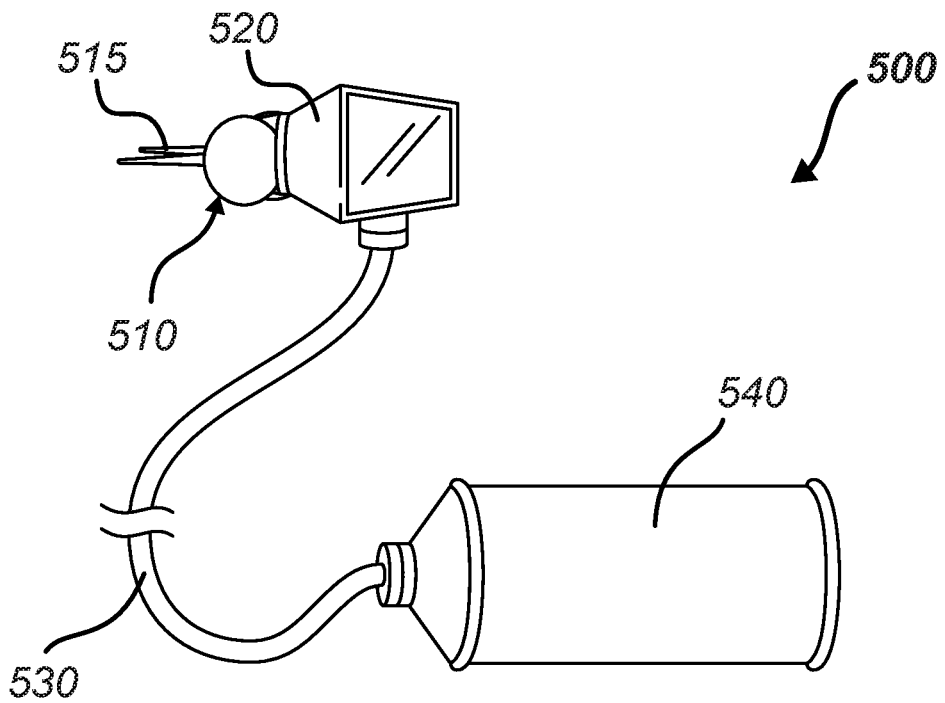
FIG. 5 depicts an otoscope having a forceps speculum attached thereto according to an embodiment of the present disclosure.

Referring to FIG. 5, embodiments of an otoscope 500 comprise a speculum 510 attached to an otoscope head 520. Flexible cable 530 provides electrical power to otoscope head 520 from handle 540, which comprises a power source. In embodiments, a power source may include one or more rechargeable and/or disposable battery cells, a power adapter connected to a wall outlet, or combinations thereof. Cable 530 allows a healthcare provider to conveniently grasp otoscope head 520 and use forceps 515 to perform fine movements by using the thumb and index finger while handling the device. In other examples, the healthcare provider may use the thumb and another finger to manipulate the forceps 515 while handling the otoscope head 520.

According to embodiments, operation of the otoscope head 520 may result in more accurate, delicate, and/or precise movements by a healthcare provider, in comparison to usage of a traditional otoscope having a power source in its handle. A healthcare provider using an otoscope head 520 may be able to carry out operations such as debridement and other scraping operations, foreign object removal, and the like with increased convenience and comfort. Such use of an otoscope head 520 having a power source connected by flexible cable 530 may result in less strain in comparison to similar uses with a relatively heavy power source integrated with the otoscope handle.

In embodiments, cable 530 can be of virtually any practical length, which may be determined according to individual preferences or specific anticipated uses of otoscope 500. One embodiment of the present disclosure has no handle, but comprises a power cable that connects directly to a power outlet or other power source. In one embodiment, a power source, such as one or more battery cells, is disposed within an otoscope head. According to various embodiments, the healthcare provider may disconnect cable 530 to reconnect the otoscope handle directly to otoscope head 520. In this configuration, the healthcare provider may use the otoscope as a typical otoscope would be used.

Figure 6:
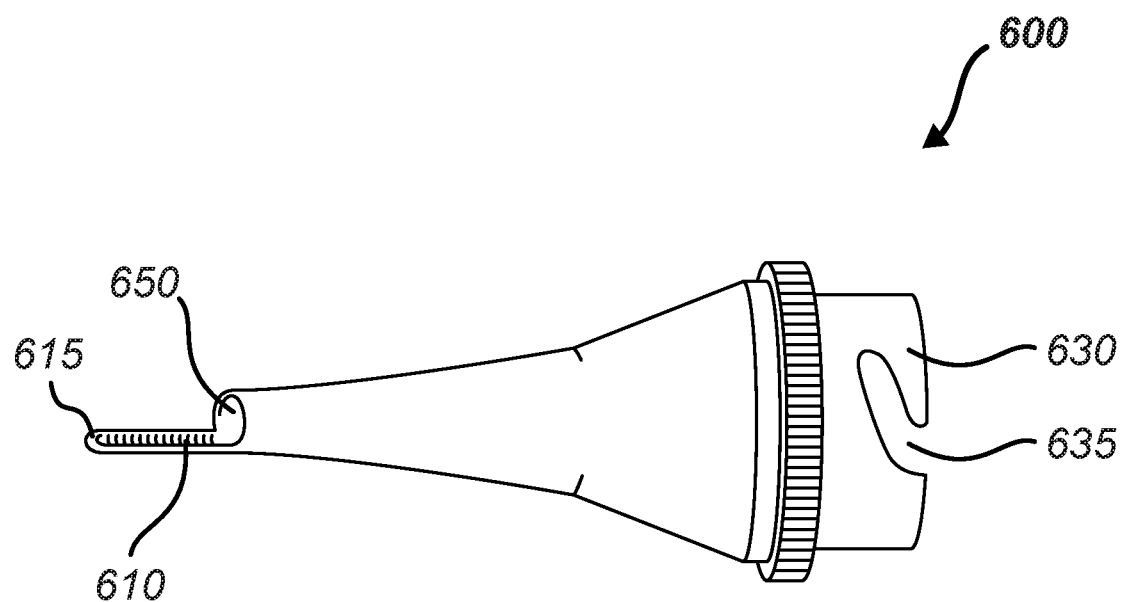
FIG. 6 depicts a perspective view of an otoscope attachment comprising a curette according to an embodiment of the present disclosure.
Figure 7:
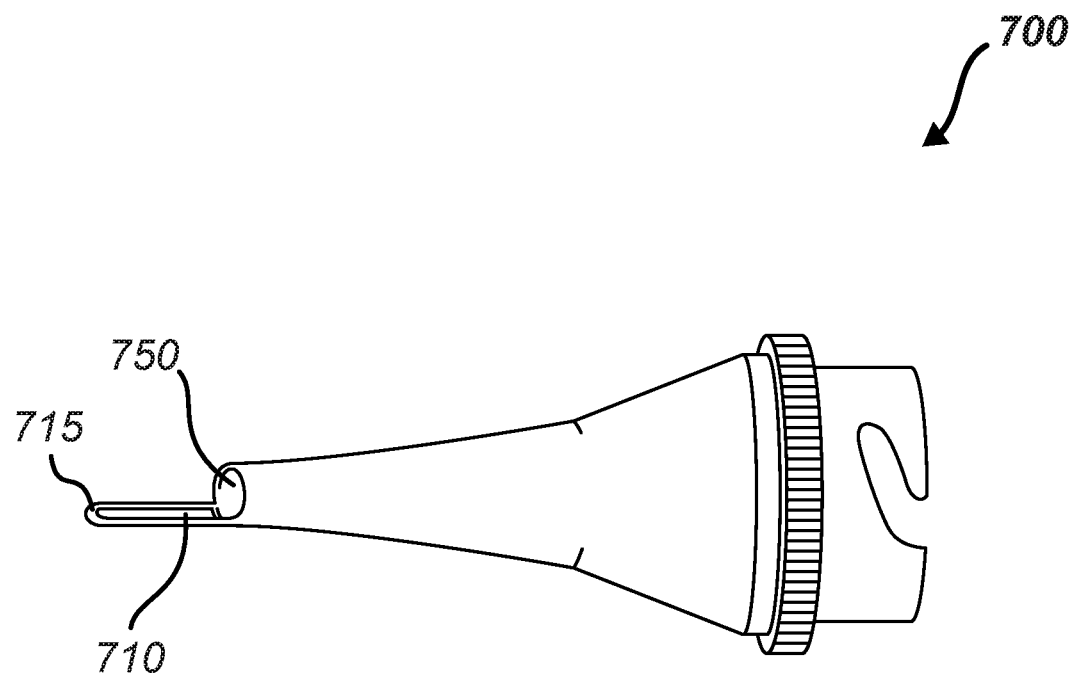
FIG. 7 depicts a profile view of an otoscope attachment comprising a curette according to an embodiment of the present disclosure.

Referring to FIG. 6, embodiments of specula 600 include a curette 610. Curette 610 comprises a scraping tip 615. In various embodiments, scraping tip 615 can be made in many different shapes according to particular intended uses or needs. As described above with respect to specula 100 and 200, one embodiment of speculum 600 comprises attachment end 630 for securing speculum 600 to an otoscope head. Attachment end 630 comprises helical attachment slits 635 for engagement with corresponding projections on an otoscope. Referring now to FIG. 7, speculum 700 comprises a curette 710 having scraping loop 715. Embodiments of specula 100, 200, 300, 400, 510, 600, or 700 include a view-hole 150, 250, 350, 450, 650, 750 to allow a healthcare provider to view through the otoscope.

In operation, embodiments of specula disclosed herein may be used by to assist a healthcare provider in examining and/or treating a patient. According to embodiments, an otoscope having a curette or forceps attached thereto may be used to remove an obstruction or other foreign body from a patient's ear or other orifice. The healthcare provider may select to use a forceps speculum, a curette speculum, or other type of attachment to an otoscope depending on the type of treatment called for. As used herein, the term "speculum instrument" may refer to forceps, a curette, or other type of implement attached to and/or integrated with an otoscope speculum.

While using a speculum with forceps, a healthcare provider may insert the forceps jaws into the patient's ear while looking through the otoscope lens. In embodiments, the healthcare provider may gently pull the patient's ear up and back to straighten the patient's ear canal. The otoscope light may be activated to illuminate the orifice. In an embodiment having a flexible power cable connecting the otoscope head to the handle and/or power source, the healthcare provider may use one hand to grasp the otoscope while the handle and/or power source is connected via a power cable and remains placed on a surface, mounted on a wall, or otherwise set in a nearby location. In embodiments, the healthcare provider can grasp the speculum and thereby hold the attached otoscope head.

In one embodiment, the healthcare provider can continue looking through the otoscope lens while guiding the forceps jaws into the patient's ear or other orifice. The healthcare provider may examine the ear or other orifice, watching for any obstructions and/or foreign bodies, without engaging the forceps jaws. In some cases, the healthcare provider may determine that there is no foreign body and extraction is not called for. In other cases, the healthcare provider may identify that an obstruction should preferably be removed. In such cases, the healthcare provider can gently guide the forceps jaws to the obstruction, squeeze the forceps to engage the clamping surface of the forceps jaws with the obstruction, and pull the obstruction out. Because of the concave inner surface of each arm of the forceps jaws, the healthcare provider may continue looking through the otoscope lens during the extraction process. After removing the foreign body, the healthcare provider may extract any additional foreign bodies.

In situations where a healthcare provider chooses to use a curette to scrape away an obstruction and/or a foreign substance from a patient's orifice, an embodiment of the present disclosure that comprises an otoscope having a curette speculum may be used. The healthcare provider may guide the curette into the patient's ear or other orifice while watching through the otoscope lens. Once the tip of the curette has reached the targeted obstruction and/or foreign substance, the healthcare provider may user the curette to scrape the obstruction and/or foreign substance by gently moving the otoscope head to which the curette speculum is attached. The healthcare provider may continue to scrape until the obstruction and/or foreign substance has been removed to the satisfaction of the healthcare provider.

In certain situations, a healthcare provider may choose to use a curette speculum to scrape a foreign body in a patient's orifice, then switch to a speculum having forceps to remove the foreign body. Additional attachments to an otoscope speculum can also likewise be utilized. Further, other treatments may be used in conjunction with embodiments of the present disclosure. For example, warm water or other liquid may be introduced to irrigate a patent's ear canal to soften an obstruction prior to removal. Embodiments of the present disclosure may be adapted to remove foreign bodies such as ear wax or insects.

Figure 8:
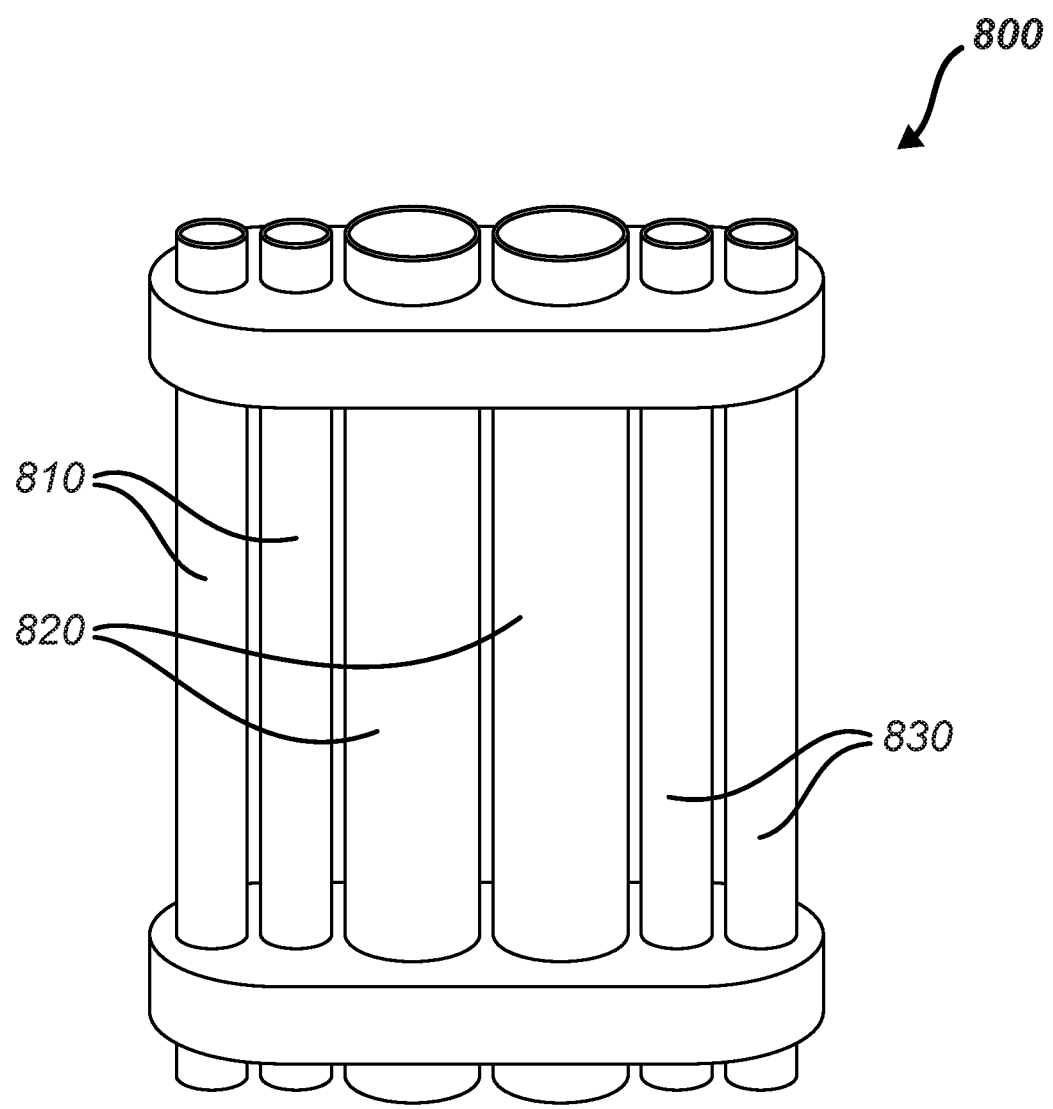
FIG. 8 depicts a speculum dispenser according to one embodiment of the present disclosure.

In embodiments, specula may be disposable after a single use. Such specula may be dispensed from a dispenser 800 as set forth in FIG. 8. Various types of specula may be stacked in corresponding dispenser tubes 810, 820, 830, from which a healthcare provider may easily remove the selected type. For example, in one embodiment, standard child-size specula may be stacked in and dispensed from tubes 810, forceps specula and curette specula may each be stacked in and dispensed from one of tubes 820, and standard adult-size specula may be stacked in and dispensed from tubes 830. In some embodiments, specula may be inserted at the top of tubes 810, 820, 830 and removed from the bottom of each tube 810, 820, 830 immediately prior to use.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the spirit and scope of the present disclosure.

What is claimed is:

1. An otoscope speculum, comprising:
   a speculum instrument comprising forceps projecting from a distal end of the speculum;
   an otoscope attachment end at a proximal end of the speculum; and
   a view-hole passing from the proximal end of the speculum to the distal end of the speculum; wherein:
   the forceps comprises a pair of opposed forceps jaws connected by a flexible hinge.

2. The otoscope speculum of claim 1, wherein each one of the pair of opposed forceps jaws comprises an inward-facing concave surface.

3. The otoscope speculum of claim 1, wherein each one of the pair of opposed forceps jaws comprises a finger squeeze grip plate.

4. An otoscope comprising:
   an otoscope head comprising a light source, a magnifying lens, and a speculum attachment point; and
   a flexible power cord adapted to supply electrical power to the otoscope head;
   an otoscope speculum attached to the speculum attachment point, the otoscope speculum comprising:
   a speculum instrument projecting from a distal end of the speculum;
   an otoscope attachment end at a proximal end of the speculum, the attachment end being attached to the speculum attachment point; and
   a view-hole passing from the proximal end of the speculum to the distal end of the speculum.

5. The otoscope speculum of claim 4, wherein the speculum instrument comprises forceps.

6. The otoscope speculum of claim 4, wherein the speculum instrument comprises a curette.

7. The otoscope speculum of claim 4, wherein the speculum instrument comprises a scraping loop.

8. A method of treating a patient, comprising:
   attaching a speculum to an otoscope head, the speculum comprising a speculum instrument;
   guiding the speculum instrument into an orifice of a patient while viewing the orifice through an otoscope lens while holding the otoscope head with only a single hand;
   with the single hand, actuating the speculum instrument on an obstruction within the orifice while viewing the obstruction through the otoscope lens;
   removing at least a part of the obstruction from the orifice; and
   removing the speculum instrument from the orifice.

9. The method of claim 8, wherein the speculum instrument comprises forceps.

10. The method of claim 9, wherein actuating the speculum instrument further comprises:
    guiding a forceps jaw to the obstruction; and
    closing the forceps jaw, thereby causing the forceps jaw to clamp on a portion of the obstruction.

11. The method of claim 8, wherein the speculum instrument comprises a curette.

12. The method of claim 11, wherein actuating the speculum instrument further comprises moving the otoscope head relative to the orifice, thereby causing the curette to scrape a portion of the obstruction.

13. The method of claim 8, wherein the speculum instrument comprises a scraping loop.

14. The method of claim 8, wherein viewing the obstruction through the otoscope lens further comprises viewing the obstruction through a view-hole of the speculum.

15. The method of claim 8, wherein the otoscope head is connected to a power source via a flexible power cable, the method further comprising grasping the otoscope head in a single hand.

\* \* \* \* \*